(12) United States Patent
Fatemi et al.

(10) Patent No.: US 9,345,448 B2
(45) Date of Patent: May 24, 2016

(54) SYSTEM AND METHOD FOR NON-INVASIVE DETERMINATION OF TISSUE WALL VISCOELASTICITY USING ULTRASOUND VIBROMETRY

(71) Applicant: Mayo Foundation for Medical Education and Research, Rochester, MN (US)

(72) Inventors: Mostafa Fatemi, Rochester, MN (US); Ivan Z. Nenadic, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 91 days.

(21) Appl. No.: 14/242,388

(22) Filed: Apr. 1, 2014

(65) Prior Publication Data

US 2014/0296709 A1    Oct. 2, 2014

Related U.S. Application Data

(60) Provisional application No. 61/807,220, filed on Apr. 1, 2013.

(51) Int. Cl.
*A61B 8/14*      (2006.01)
*A61B 8/08*      (2006.01)

(52) U.S. Cl.
CPC .............. *A61B 8/0858* (2013.01); *A61B 8/485* (2013.01); *A61B 8/5223* (2013.01)

(58) Field of Classification Search
CPC ..... A61B 8/0858; A61B 8/485; A61B 8/5223
See application file for complete search history.

(56) References Cited

U.S. PATENT DOCUMENTS

2010/0198075 A1    8/2010 McMorrow et al.

OTHER PUBLICATIONS

Nenadic, et al., "Lamb Wave Dispersion Ultrasound Vibrometry (LDUV) Method for Quantifying Mechanical Properties of Viscoelastic Solids", Physics in Medicine and Biology, Phys. Med. Biol. 56, 2011, pp. 2245-2264.
Nenadic, et al., Measurements of Viscoelasticity using the MR Elastography and Lamb wave Dispersion Ultrasound Vibrometry (LDUV), IEEE International Ultrasonics Symposium Proceedings, 2011, pp. 1167-1170.
Kanai, et al., "Propagation of Spontaneously Actuated Pulsive Vibration in Human Heart Wall and In Vivo Viscoelasticity Estimation", IEEE Transactions on Ultrasonics, Ferroelectrics, and Frequency Control, vol. 52 No. 11, Nov. 2005, pp. 1931-1942.
Watanabe et al., "Comparative Anaylsis of Bladder Wall Compliance Based on Cystometry and Biosensor Measurements During the Micturition Cycle of the Rat", Neurourology and Urodynamics 16, 1997, pp. 567-581.

*Primary Examiner* — Mark Remaly
(74) *Attorney, Agent, or Firm* — Yakov Sidorin; Quarles & Brady, LLP

(57) ABSTRACT

System and method for determining viscoelasticity of curved tissue walls using ultrasound bladder vibrometry (UBV). The UBV is a non-invasive technique utilizing, in a specific case, a focused ultrasound radiation force to excite Lamb waves in a curved bladder wall and pulse-echo techniques to track the tissue deformation propagating through such curved wall. Cross-spectral analysis is used to calculate the wave velocity, which is directly related to the elastic properties of the bladder wall.

11 Claims, 13 Drawing Sheets

SYSTEM AND METHOD FOR NON-INVASIVE DETERMINATION OF TISSUE WALL VISCOELASTICITY USING ULTRASOUND VIBROMETRY

CROSS-REFERENCE TO RELATED APPLICATIONS

The present application claims priority form and benefit of U.S. Provisional Patent Application No. 61/807,220 filed on Apr. 1, 2013 and titled "System and Method for Non-Invasive Determination of Tissue Wall Viscoelasticity Using Ultrasound Vibrometry". The disclosure of the above-identified patent application is incorporated herein by reference in its entirety.

BACKGROUND OF THE INVENTION

The present invention relates to systems and methods for analyzing tissue structure and function. More particularly, the invention relates to a method for determining tissue wall viscoelasticity, such as viscoelasticity of a bladder wall, using ultrasound vibrometry to excite mechanical waves in the bladder wall and track the motion using ultrasound pulse-echo techniques.

An elastic bladder is important for storing increasing volumes of urine at low pressures. Increases in bladder elasticity (bladder stiffening) resulting in bladder dysfunction are associated with age and pathogenic processes, and are largely due to an increase in connective tissue relative to the smooth muscle in the bladder wall. A variety of congenital conditions such as urethral defects and neuropathic conditions (i.e. myelomeningocele), and conditions such as spinal cord trauma, tumors, or obstructive uropathy are associated with bladder dysfunction. As the percent of connective tissue increases compared to smooth muscle, the bladder becomes more rigid, and is less able to expand during filling. This can result in decreased bladder capacity, which may manifest in lower urinary tract symptoms, including incontinence. Reduced bladder compliance (defined as changes in bladder volume due to a change in the detrusor muscle pressure) is of particular importance in subpopulations of patients with neurogenic bladder disorders who must be carefully monitored with urodynamic studies (UDS) on an annual basis to ensure that bladder pressures stay within normal parameters.

Urodynamic studies are currently considered the gold standard in clinical assessment for measuring bladder compliance, but are uncomfortable and carry risks of infection. A typical procedure lasts approximately 45 minutes, requires catheter placement in the bladder and the vagina or rectum, filling the bladder at a defined rate, and measuring the change in $P_{det}$ defined as detrusor pressure as the bladder fills. A compliant (elastic) bladder expands to accommodate the filling volume, resulting in a low detrusor pressure, while a non-compliant (inelastic) bladder does not expand as readily and the detrusor pressure rises during bladder filling. The urodynamic studies are often accompanied by pain during and following the procedure, traumas and infection due to urinary catheterization have been reported in both men and women. In addition to discomfort and clinical risks, urodynamic studies are labor and resource intensive for the institutions that treat and follow these patients.

Several ultrasound-based studies have noted that the bladder wall thickness (BWT) and total bladder weight increases in animal models of intravesical obstruction. Increases in BWT have been attributed to increased fibrosis in the bladder as the result of aging or pathogenic processes. Increased thickening of the bladder wall corresponds to increases in bladder weight, both of which may correspond to a reduction in bladder elasticity and decline in bladder function. Ultrasound methods have therefore been adapted to measure BWT, bladder surface area, and total estimated bladder weight, and are currently being examined as potential non-invasive measures of bladder structure and function. These ultrasound measurements of bladder weight and wall thickness provide indirect measures of structural changes. That is, these methods rely on metrics, such as BWT, bladder surface area, and bladder weight as metrics that can be indirectly correlated with bladder functionality or structure. Regardless of the cause of dysfunction, the structure, thickness and biomechanics of the bladder wall can be altered significantly. However, these and other available techniques do not provide a non-invasive and relatively pain-free, quantitative measurement of bladder elasticity. Instead, in clinical practice, clinicians must rely on urodynamic studies despite the above-described risks and drawbacks.

Therefore, there is a need for systems and methods to non-invasively and painlessly provide salient information regarding the mechanical properties of the bladder wall in patients who experience bladder dysfunction.

SUMMARY

The present invention overcomes the aforementioned drawbacks by providing a system and method that is relatively pain-free and non-invasively determines viscoelasticity of the bladder, using ultrasound bladder vibrometry (UBV). The present invention further overcomes the aforementioned drawbacks by providing a system and method that can be used for early evaluation and more frequent follow-ups of patients who experience incontinence. UBV is a non-invasive technique that uses ultrasound radiation force that is focused to excite Lamb waves in wall and pulse-echo techniques to track the tissue deformation. In this regard, the term "bladder" may not refer to the "urinary" bladder in the human body, but may, more generally, refer to a tissue volume formed by tissue walls that may have some elasticity. Accordingly, the urinary bladder is one example of a bladder. Cross-spectral analysis can be used to calculate the wave velocity, which is related to the elastic properties of the bladder wall.

In accordance with one aspect of the invention, a system and method for non-invasively determining viscoelasticity of an elastic tissue volume using ultrasound vibrometry is disclosed. The system uses ultrasound radiation force to "tap" the wall of the elastic tissue volume and excite Lamb waves. The system further includes using pulse-echo ultrasound to track the motion of the wall. Fourier space analysis of the tissue motion is used to obtain the wave velocity dispersion (change of wave velocity as a function of frequency). An analytical Lamb wave model is fit to the dispersion data to estimate viscoelasticity of the elastic tissue volume.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

Figure 1:
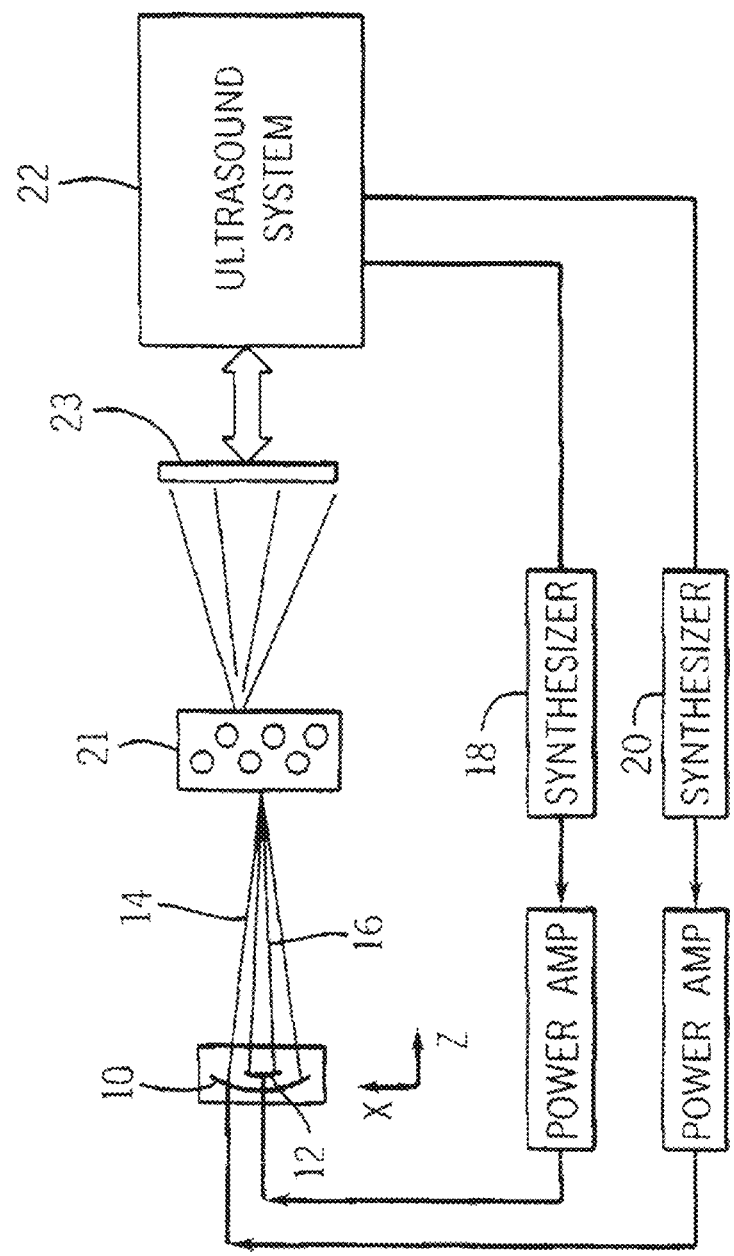
FIG. 1 is a block diagram of a vibro-acoustic system.

Ultrasound elastography methods have been used to measure elasticity of various soft tissues. During the past decade, several techniques based on acoustic radiation force (ARF) have been developed to study tissue elasticity. Supersonic shear imaging uses ARF to induce a shear wave in tissue and produce a map of shear elastic modulus of the tissue. More recently, Shearwave Dispersion Ultrasound Vibrometry (SDUV) has been developed for measuring tissue elasticity and viscosity.

The above techniques are generally designed assuming wave propagation in the bulk tissue (theoretically without boundaries), for applications in organs such as breast, liver, kidney, muscle and prostate. The above techniques also assume that the tissue being examined is infinitely thick. However, this assumption is not appropriate for bladders, where the expected bladder wall thickness would be at most a few millimeters. Additionally, current models in the above-mentioned methods are not appropriate for the unique properties of the bladder, as the bladder wall serves as the interface between a liquid (internally) and the rest of the body cavity (externally).

Recent studies have investigated the use of Lamb wave Dispersion Ultrasound Vibrometry (LDUV) to non-invasively quantify viscoelasticity of plate-like organs, such as the heart wall. LDUV is an SDUV-based technique that uses a mechanical actuator or ultrasound radiation force that is focused to excite Lamb waves in the medium of interest and a pulse echo transducer to track the deformation and estimate phase velocity. The Lamb wave dispersion equation is fitted to the measured Lamb wave velocity dispersion (change in phase velocity as a function of frequency) to estimate elasticity and viscosity of the medium. However, the Lamb wave dispersion equation used in LDUV assumes a flat plate model and that the plate is surrounded by water-like fluid (urine, blood, pericardial fluid, etc.) on both sides. The bladder, on the other hand, has a wall that is spatially curved and (a curved plate) and contains urine on one side, but is surrounded by connective tissue, fat and peritoneal fluid on the superficial side. Therefore, the conventionally-used LDUV technique cannot be readily applied to the bladder.

Other methods for measuring mechanical properties of the bladder, such as stiffness, include using a biosensor that directly evaluates the properties of the bladder wall. Stiffness measurements made using the biosensor can be considered to represent the instantaneous biomechanical properties of the bladder wall. The measurements can be obtained whether the bladder is empty, filling, or spontaneously contracting. Evidently, since the measurements are made only at the region of the bladder wall where the biosensor makes contact, the resulting stiffness data are more specific to that region and may be used to examine regional inhomogeneity. Although the biosensor provides a direct measure of bladder stiffness, the biosensor is mounted on a catheter that comes in contact with the bladder tissue whose stiffness is to be measured, thereby still providing an invasive procedure for the patient.

Referring particularly to FIG. 1, a vibro-acoustography system that employs the present invention includes an ultrasonic transducer having two elements 10 and 12, which produce two focused beams 14 and 16 that cross each other at their focal points. The elements 10 and 12 are driven by respective continuous wave synthesizers 18 and 20 at ultrasonic frequencies $\omega_1$ and $\omega_2$ that differ by a desired beat frequency. The two focused beams 14 and 16 are aimed at target tissue 21 that is to be measured, and in response, the target tissue vibrates, or oscillates, at the difference frequency. These elements thus serve as a force generator that oscillates the target tissues 21 at a prescribed beat frequency.

The vibrations of the target tissue 21 are measured by an ultrasound system 22. As will be described in more detail below, the ultrasound system 22 drives an ultrasonic transducer 23 to apply a focused or unfocused ultrasound beam to the target tissue 21 and to receive the echo signal reflected by the target tissue 21. The phase and amplitude of these echo signals are processed as described below to measure mechanical properties of the target tissue 21.

Figure 2:
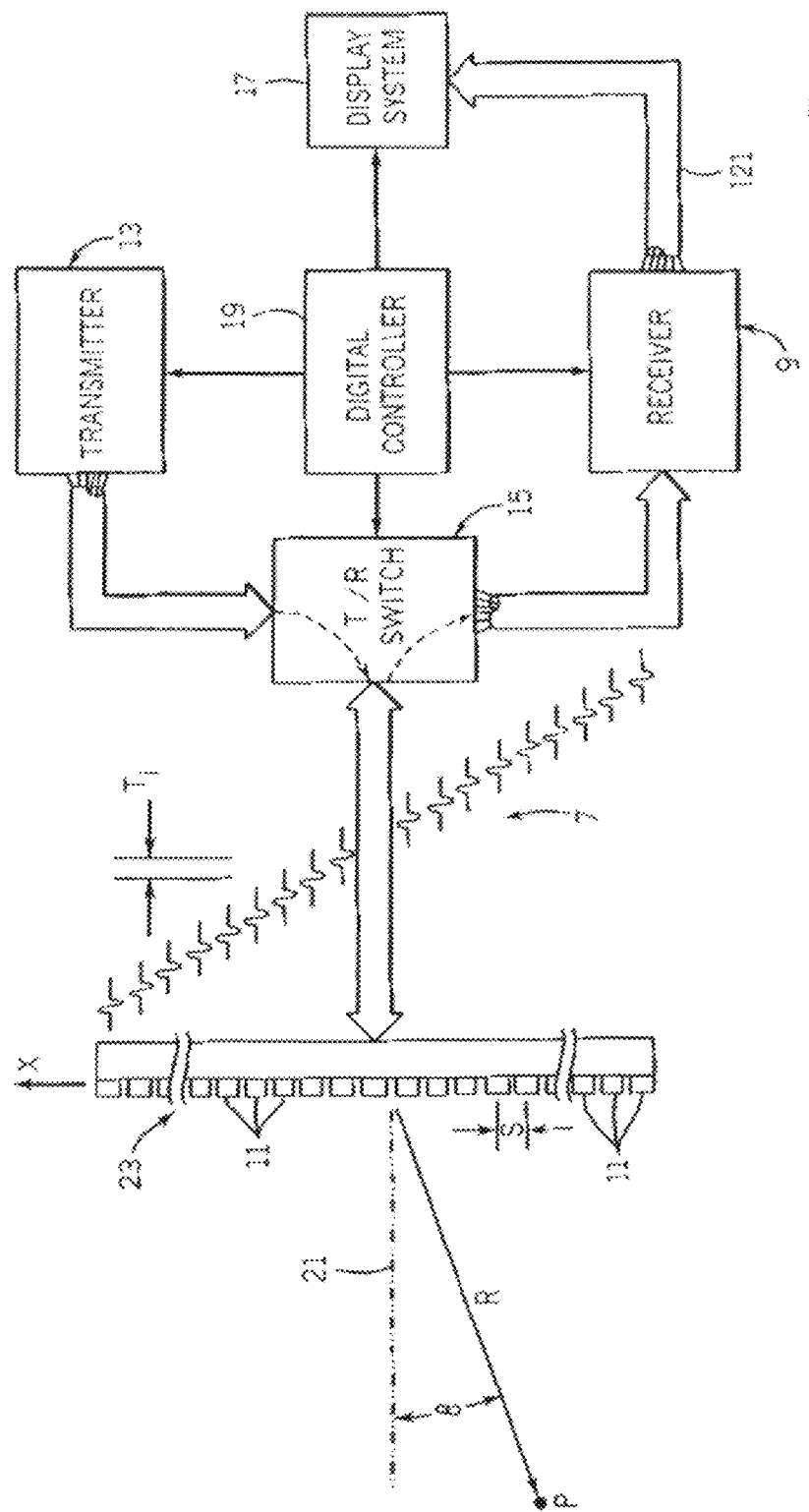
FIG. 2 is a block diagram of an ultrasound imaging system used in the system of FIG. 1.

Referring particularly to FIG. 2, a transducer array 23 includes a plurality of separately driven elements 11 that each produce a burst of ultrasonic energy when energized by a pulse produced by a transmitter 13. The ultrasonic energy reflected back to the transducer array 23 from the subject under study is converted to an electrical signal by each transducer element 11 and applied separately to a receiver 9 through a set of switches 15. The transmitter 13, receiver 9 and the switches 15 are operated under the control of a digital controller 19 responsive to the commands input by the human operator. A complete scan is performed by acquiring a series of echoes in which the switches 15 are set to their transmit position, the transmitter 13 is gated on momentarily to energize each transducer element 11, the switches 15 are then set to their receive position, and the subsequent echo signals produced by each transducer element 11 are applied to the receiver 9. The separate echo signals from each transducer element 11 are combined in the receiver 9 to produce a single echo signal that is employed to produce a line in an image on a display system 17.

The transmitter 13 drives the transducer array 23 such that the ultrasonic energy produced is directed, or steered, in a beam or pulse. A B-scan can therefore be performed by moving this beam through a set of angles from point-to-point rather than physically moving the transducer array 23. To accomplish this, the transmitter 13 imparts a time delay (Ti) to the respective pulses 20 that are applied to successive transducer elements 11. If the time delay is zero (Ti=0), all the transducer elements 11 are energized simultaneously and the resulting ultrasonic beam is directed along an axis 21 normal to the transducer face and originating from the center of the transducer array 23. As the time delay (Ti) is increased, the ultrasonic beam is directed downward from the central axis 21 by an angle θ.

A sector scan is performed by progressively changing the time delays Ti in successive excitations. The angle θ is thus changed in increments to steer the transmitted beam in a succession of directions. When the direction of the beam is above the central axis 21, the timing of the pulses 7 is reversed.

Referring still to FIG. 2, the echo signals produced by each burst of ultrasonic energy emanate from reflecting objects located at successive positions (R) along the ultrasonic beam. These are sensed separately by each segment 11 of the transducer array 23 and a sample of the magnitude of the echo signal at a particular point in time represents the amount of reflection occurring at a specific range (R). Due to the differences in the propagation paths between a focal point P and each transducer element 11, however, these echo signals will not occur simultaneously and their amplitudes will not be equal. The function of the receiver 9 is to amplify and demodulate these separate echo signals, impart the proper time delay to each and sum them together to provide a single echo signal that accurately indicates the total ultrasonic energy reflected from each focal point P located at range R along the ultrasonic beam oriented at the angle θ.

To simultaneously sum the electrical signals produced by the echoes from each transducer element 11, time delays are introduced into each separate transducer element channel of the receiver 9. In the case of the linear array 23, the delay introduced in each channel may be divided into two components, one component is referred to as a beam steering time delay, and the other component is referred to as a beam focusing time delay. The beam steering and beam focusing time delays for reception are precisely the same delays (Ti) as the transmission delays described above. However, the focusing time delay component introduced into each receiver channel is continuously changing during reception of the echo to provide dynamic focusing of the received beam at the range R from which the echo signal emanates.

Under the direction of the digital controller 19, the receiver 9 provides delays during the scan such that the steering of the receiver 9 tracks with the direction of the beam steered by the transmitter 13 and it samples the echo signals at a succession of ranges and provides the proper delays to dynamically focus at points P along the beam. Thus, each emission of an ultrasonic pulse results in the acquisition of a series of data points that represent the amount of reflected sound from a corresponding series of points P located along the ultrasonic beam.

By selecting proper time delays, echoes from multiple focused locations can be received to measure vibration information from several points of the tissue. The limitation of the lateral resolution of the transducer for two closely located points can be improved by assigning different transmitting codes for different locations.

The display system 17 receives the series of data points produced by the receiver 9 and converts the data to a form producing the desired image. For example, if an A-scan is desired, the magnitude of the series of data points is merely graphed as a function of time. If a B-scan is desired, each data point in the series is used to control the brightness of a pixel in the image, and a scan comprised of a series of measurements at successive steering angles (θ) is performed to provide the data necessary for display of an image.

Figure 3:
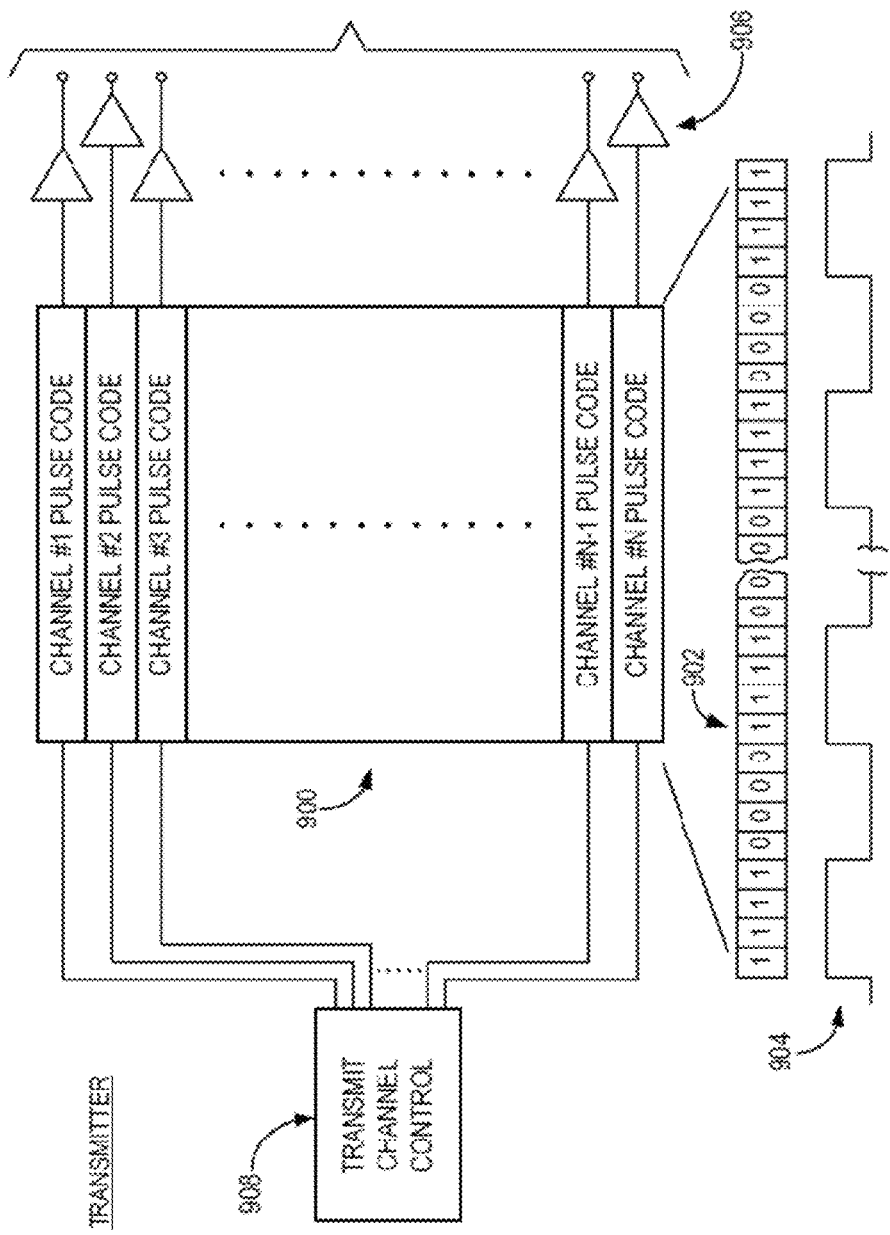
FIG. 3 is a block diagram of a transmitter that forms part of the ultrasound imaging system of FIG. 2.

Referring particularly to FIG. 3, the transmitter 13 includes a set of channel pulse code memories that are indicated collectively at 900. Each pulse code memory 900 stores a bit pattern 902 that determines the frequency of the ultrasonic pulse 904 that is to be produced. This bit pattern is read out of each pulse code memory 900 by a master clock and applied to a driver 906 that amplifies the signal to a power level suitable for driving the transducer 23. In the example shown in FIG. 3, the bit pattern is a sequence of four "1" bits alternated with four "0" bits to produce a 5 megahertz ("MHz") ultrasonic pulse 904. The transducer elements 23 to which these ultrasonic pulses 904 are applied respond by producing ultrasonic energy.

As indicated above, to steer the transmitted beam of the ultrasonic energy in the desired manner, the pulses 904 for each of the N channels must be produced and delayed by the proper amount. These delays are provided by a transmit control 908 that receives control signals from the digital controller 19. When the control signal is received, the transmit control 908 gates a clock signal through to the first transmit channel 900. At each successive delay time interval thereafter, the clock signal is gated through to the next channel pulse code memory 900 until all the channels to be energized are producing their ultrasonic pulses 904. Each transmit channel 900 is reset after its entire bit pattern 902 has been transmitted and the transmitter 13 then waits for the next control signal from the digital controller 19.

Figure 4:
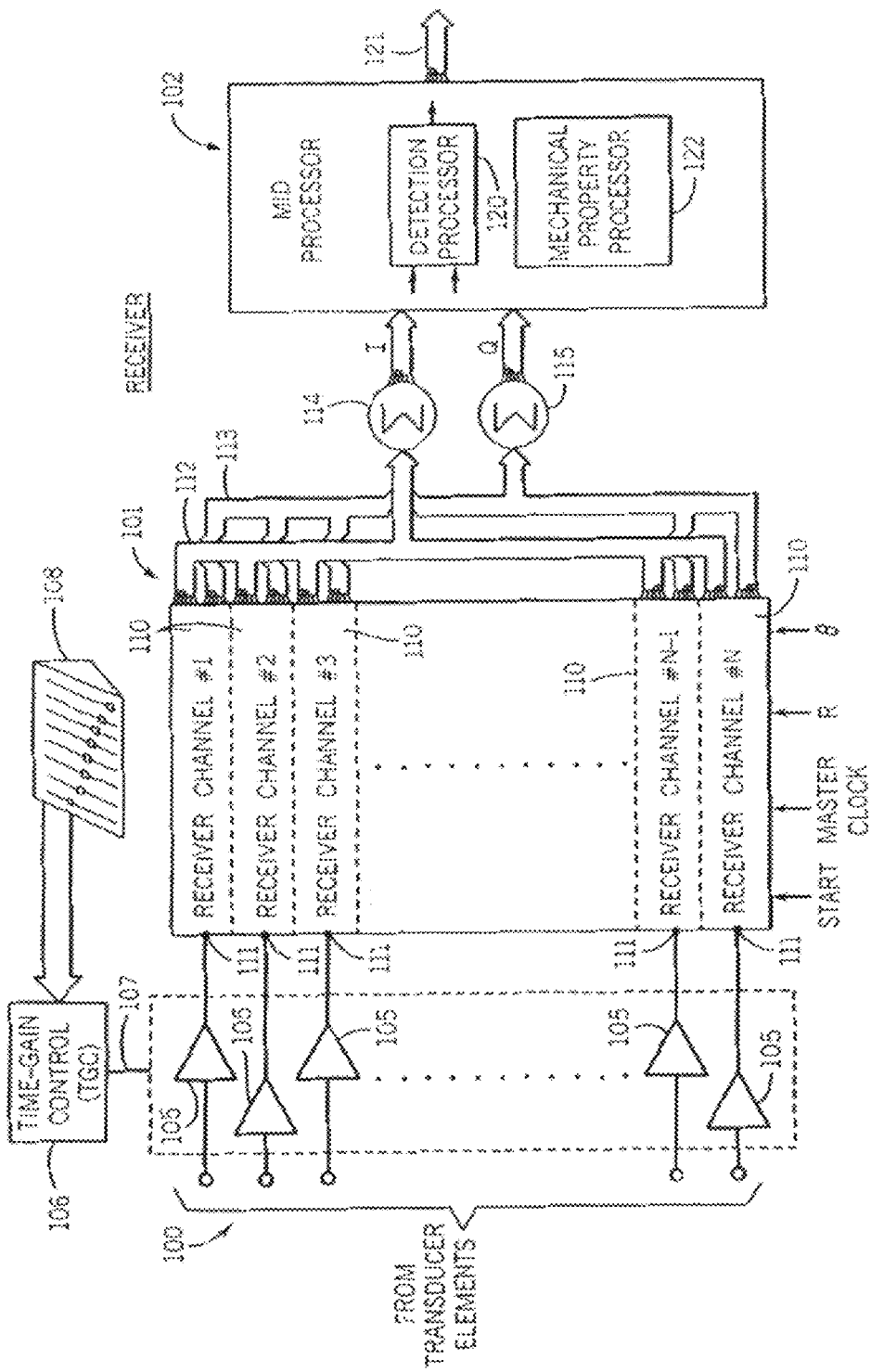
FIG. 4 is a block diagram of a receiver that forms part of the ultrasound imaging system of FIG. 2.

Referring particularly to FIG. 4, the receiver 9 is comprised of three sections: a time-gain control section 100, a beam forming section 101, and a mid processor 102. The time-gain control section 100 includes an amplifier 105 for each of the N=128 receiver channels and a time-gain control circuit 106. The input of each amplifier 105 is connected to a respective one of the transducer elements 11 to receive and amplify the echo signal that it receives. The amount of amplification provided by the amplifiers 105 is controlled through a control line 107 that is driven by the time-gain control circuit 106. As is well known in the art, as the range of the echo signal increases, its amplitude is diminished. As a result, unless the echo signal emanating from more distant reflectors is amplified more than the echo signal from nearby reflectors, the brightness of the image diminishes rapidly as a function of range (R). This amplification is controlled by the operator who manually sets TGC linear potentiometers 108 to values that provide a relatively uniform brightness over the entire range of the sector scan. The time interval over which the echo signal is acquired determines the range from which it emanates, and this time interval is divided into by the TGC control circuit 106. The settings of the potentiometers are employed to set the gain of the amplifiers 105 during each of the respective time intervals so that the echo signal is amplified in ever increasing amounts over the acquisition time interval.

The beam forming section 101 of the receiver 9 includes N=128 separate receiver channels 110. Each receiver channel 110 receives the analog echo signal from one of the TGC amplifiers 105 at an input 111, and it produces a stream of digitized output values on an I bus 112 and a Q bus 113. Each of these I and Q values represents a sample of the echo signal envelope at a specific range (R). These samples have been delayed in the manner described above such that when they are summed at summing points 114 and 115 with the I and Q samples from each of the other receiver channels 110, they indicate the magnitude and phase of the echo signal reflected from a point P located at range R on the steered beam ($\theta$).

Referring still to FIG. 4, the mid processor section 102 receives the beam samples from the summing points 114 and 115. The I and Q values of each beam sample is a 16-bit digital number that represents the in-phase and quadrature components of the magnitude of the reflected sound from a point (R, $\theta$). The mid processor 102 can perform a variety of calculations on these beam samples, where choice is determined by the type of image to be reconstructed.

For example, a conventional ultrasound image may be produced by a detection processor 120 that calculates the magnitude of the echo signal from its I and Q components:

$$M = \sqrt{I^2 + Q^2}. \tag{1}$$

The resulting magnitude values output at 121 to the display system 17 result in an image in which the magnitude of the reflected echo at each image pixel is indicated.

The present invention is implemented by a mechanical property processor 122 that forms part of the mid-processor 102. As will be explained in detail below, this processor 102 receives the I and Q beam samples acquired during a sequence of measurements of the subject tissue and calculates a mechanical property (i.e., thickness) of the tissue.

Figure 5:
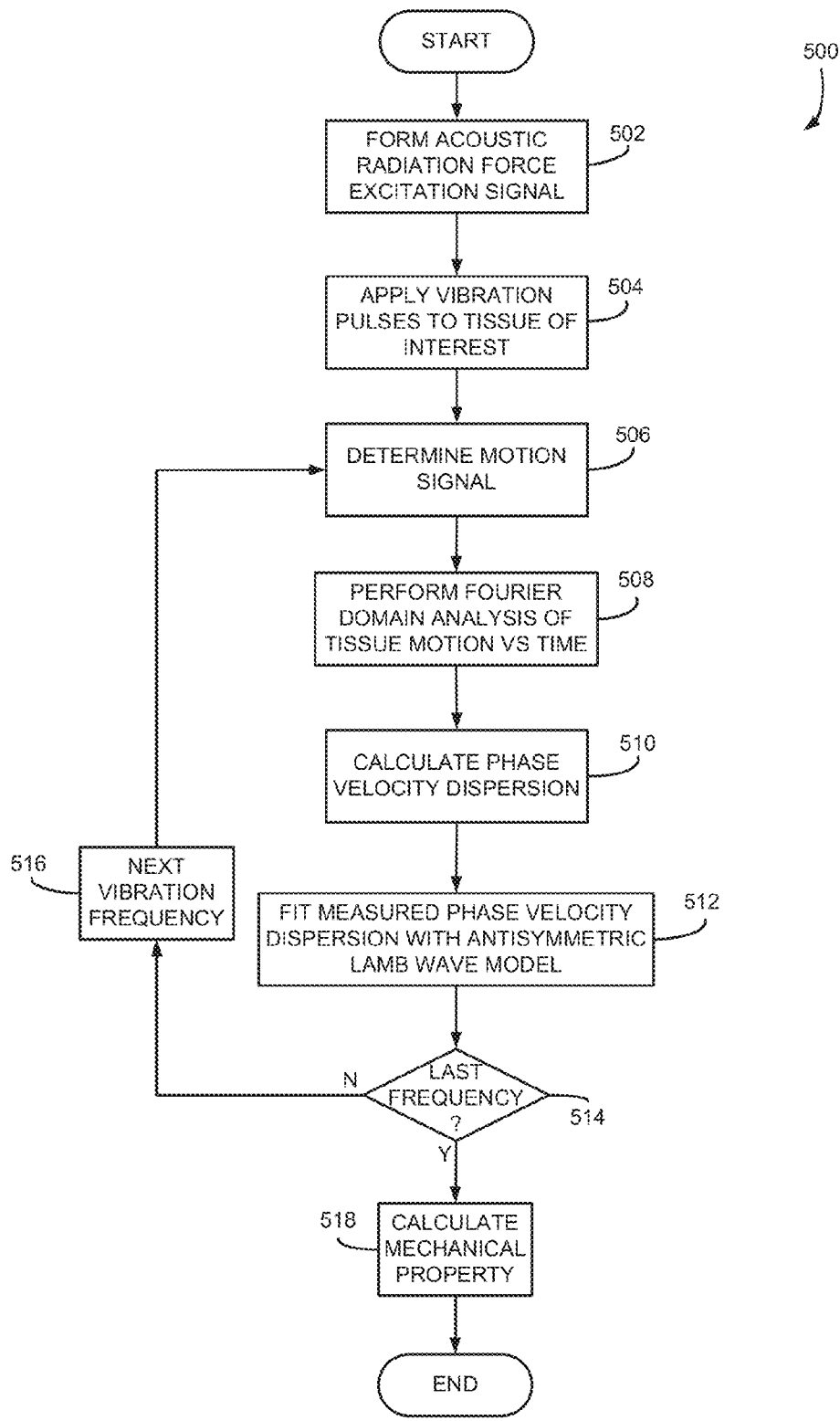
FIG. 5 is a flow chart of the steps using the ultrasound imaging system of FIG. 2 to measure one or more mechanical properties of tissue.

Referring now to FIG. 5, a flow chart is provided setting forth exemplary steps 500 of a method to measure one or more mechanical properties of tissue 21 in accordance with the present invention. The process begins at process block 502 with the formation of acoustic radiation force excitation signals that are applied, at process block 504, to a subject to, thereby, apply vibration pulses to tissue of interest. Referring to FIG. 6, a diagram of the fundamental principal of ultrasound bladder vibrometry (UBV) is shown. Again, the term "bladder" may not refer to the "urinary" bladder in the human body, but may, more generally, refer to a tissue volume formed by tissue walls that may have some elasticity. UBV uses focused ultrasound to produce a radiation force 604 (push beam) to excite impulsive Lamb waves (200-600 µs in length) in the medium of interest. The radiation force excitation 604 can be, for example, of 600 µs toneburst.

The focused ultrasound radiation force applied on a membrane-like medium, such as the bladder wall, excites cylindrical waves. The urine filled bladder can be modeled as an incompressible, homogenous, isotropic solid submerged in an incompressible non-viscous fluid, for example. The antisymmetric Lamb wave dispersion equation (2) for such geometry is as follows:

$$4k_L^2 \eta \beta \cosh(\eta h)\sinh(\beta h) - (2k_L^2 - k_s^2)^2 \sinh(\eta h)\cosh(\beta h) = \frac{\rho_1 \eta k_s^4}{\rho_2 \eta_f} \cosh(\eta h)\cosh(\beta h) \tag{2}$$

Where $$\beta = \sqrt{k_L^2 - k_s^2}, \quad \eta = \sqrt{k_L^2 - k_p^2}, \quad \eta_f = \sqrt{k_L^2 - k_f^2},$$

$k_f$ is the wave number of the compressional wave in the fluid, $k_p$ is the wave number of the compressional wave in tissue, $k_L = \omega/c_L$ is the Lamb wave number, $\omega$ is the angular frequency, $c_L$ is the frequency dependent Lamb wave velocity, $k_s = \omega\sqrt{\rho_m/\mu}$ is the shear wave number, $\rho_m$ is the density and h is the half-thickness of the bladder wall (H=2h). For the case of tissue, urine and blood, the compressional wave numbers ($k_p$ and $k_f$) are similar and much smaller than the shear and Lamb wave numbers ($k_s$) and ($k_L$), so $$\eta_f \approx \eta = \sqrt{k_L^2 - k_p^2} \approx k_L.$$

Due to similar densities of tissue, urine and blood, the dispersion equation (2) is simplified as:

$$4k_L^3 \beta \cosh(k_L h)\sinh(\beta h) - (k_s^2 - 2k_L^2)^2 \sinh(k_L h)\cosh(\beta h) = k_s^4 \cosh(k_L h)\cosh(\beta h) \tag{3}$$

Alternatively, an external mechanical vibrator (not shown) can be used to excite shear waves in the bladder. With the external mechanical vibrator, the ultrasound radiation force is not applied, and only ultrasound is used to detect the waves on the bladder wall. The mechanical vibrator may include a speaker-like mechanism with a plastic shaft that transfers the mechanical energy to the skin. The mechanical energy then vibrates the abdomen and the bladder.

Figure 6A:
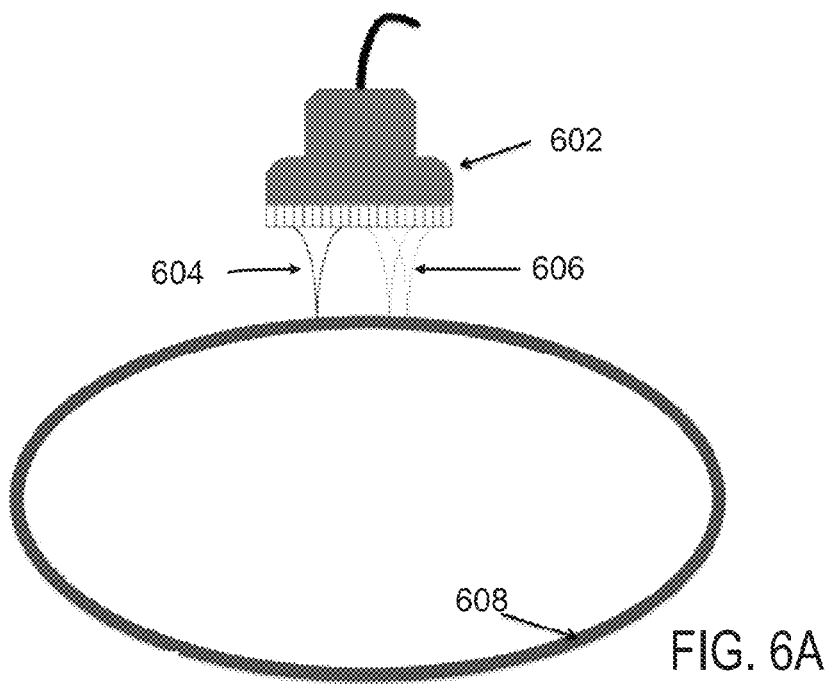
FIG. 6A is a diagram of the basic principal of ultrasound bladder vibrometry (UBV) of the present invention.
Figure 6B:
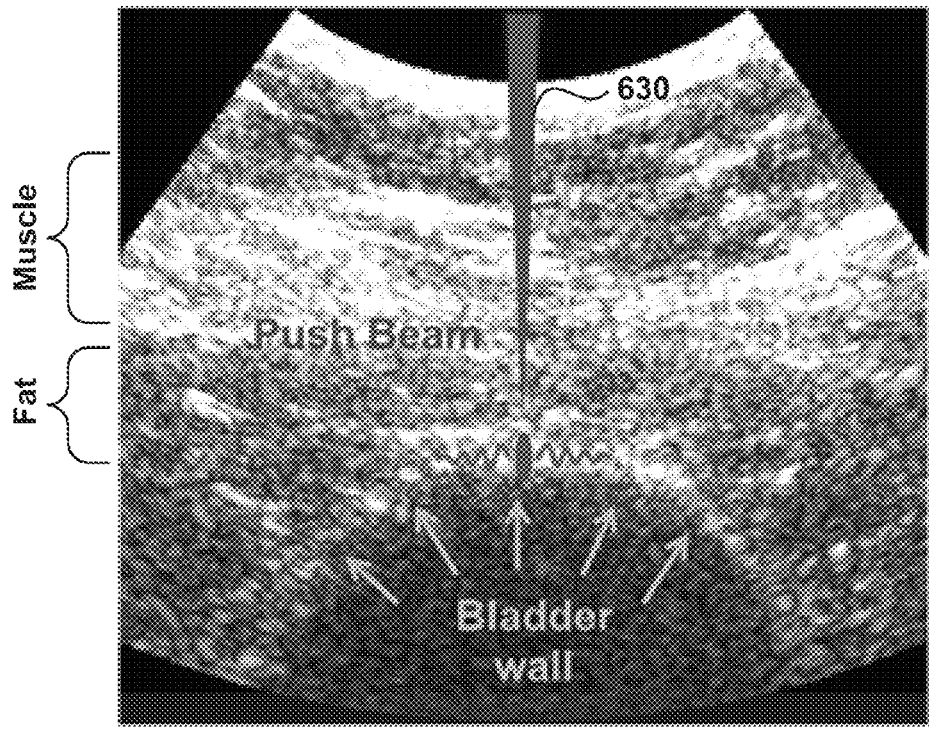
FIG. 6B illustrates in vivo human B-mode of the bladder with a sketch of the UBV excitation beam.

Referring again to FIGS. 5 and 6, at process block 506, a pulse-echo ultrasound 606 (detection beam) is used to measure the motion at several points along a line of propagation 608, the line of propagation being, for example, a bladder wall, in order to track tissue motion through successive B-modes. Though the following description is made with respect to the bladder wall, other elastic tissue volumes may likewise be considered. The B-mode scanning can be performed by, for example, a Verasonics ultrasound imaging platform equipped with a C4-2 linear array transducer 602, as shown in FIG. 6A, to excite 400-600 µs impulse in the bladder wall and track the mechanical motion. Verasonics is a registered trademark of Verasonics, Inc. Corporation of Redmond, Wash. The detection beam 606 can be transmitted with a pulse repetition frequency (PRF) of about 2.0 kHz for example (2.5 kHz in another example) with a center of frequency of about 3.0 MHz (3.3 MHz in a specific case). FIG. 6B illustrates in vivo human B-mode of the bladder with a sketch of the UBV excitation beam 630.

Cross-spectral analysis of the received echoes can then be used to calculate the bladder wall motion as a function of time. Because an impulse contains mostly the frequency components up to the inverse of the time length of the impulse, many phase velocities from a single impulse push can be extracted. As shown at process block 508, a two-dimensional fast Fourier transform (2D-FFT) of the bladder wall motion may be used to calculate the change of Lamb wave velocity as a function of frequency, or the Lamb wave dispersion. In other words, Fourier-space analysis of the motion may be used as a function of time that yields the k-space whose coordinates are frequency, f, and wave number, k. Since the wave velocity c=k/f, the phase velocity at each frequency can be calculated at process block 510 by searching for peaks at the given frequency and dividing by the wave number coordinate by the frequency coordinate for the given peak. The Lamb wave dispersion equation may be fit to the dispersion data at process block 512 to estimate bladder viscoelasticity, as shown at process block 518. As indicated by process block 514, the digital controller determines whether the last frequency has been measured when a harmonic excitation approach is used. If not, at process block 516, another frequency is selected and process blocks 506 through 512 are repeated at each desired prescribed frequency.

Figure 8:
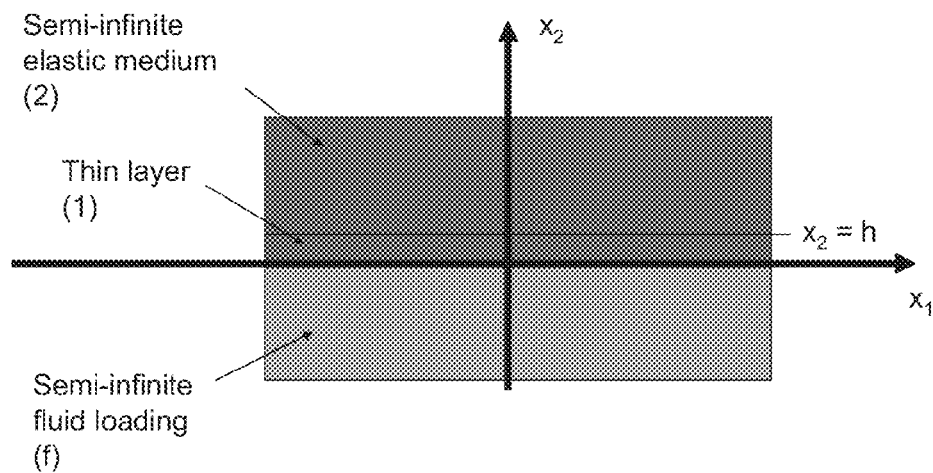
FIG. 8 is a diagram of a thin layer on a semi-infinite elastic medium and fluid loading according to one aspect of the present invention.

As discussed above, the Lamb wave model assumes that the bladder is surrounded by a fluid on both sides, which, in some situations, may not be sufficient to quantify mechanical properties of the bladder. In accordance with another aspect of the present disclosure, a more complex model can be derived to account for the fact that the bladder wall is surrounded by urine on one side and a soft connective tissue and muscle on the other. To this end, the analytical model for Lamb wave propagation can be created that includes a plate surrounded by a semi-infinite fluid on one side and a semi-infinite solid on the other, as shown in FIG. 8. This model may be advantageous because it mimics the natural surroundings of the bladder wall. The model includes a thin layer of thickness, h, in contact with a rigid half space on one side and fluid coupled to the upper surface as shown in FIG. 8. The potential functions for the wave motion can be described as follows:

$$\phi_1 = (a_1 e^{-i\eta_1 x_2} + b_1 e^{i\eta_1 x_2})e^{ikx_1} \quad (4)$$

$$\psi_1 = (c_1 e^{-i\beta_1 x_2} + d_1 e^{i\beta_1 x_2})e^{ikx_1}$$

$$\phi_2 = b_2 e^{-\eta_2 x_2} e^{ikx_1}$$

$$\psi_2 = d_2 e^{-\beta_2 x_2} e^{ikx_1}$$

$$\phi_f = m e^{\eta_f x_2} e^{ikx_1}$$

where $$\eta_1 = \sqrt{k_{p1}^2 - k^2}, \ \beta_1 = \sqrt{k_{s1}^2 - k^2}, \ \eta_2 = \sqrt{k^2 - k_{p2}^2},$$

$$\beta_2 = \sqrt{k^2 - k_{s1}^2}, \ \eta_f = \sqrt{k^2 - k_f^2},$$

and k is the wave number, a subscript p denotes the primary or compression wave, a s subscript denotes the shear wave, f denotes the fluid. The following boundary conditions can be applied at $x_2$=h:

$$\sigma_{22}^1 = \sigma_{22}^2$$

$$\sigma_{12}^1 = \sigma_{12}^2$$

$$u_1^1 = u_1^2$$

$$u_2^1 = u_2^2, \quad (5)$$

and the following boundary conditions at the interface between the layer and rigid half-space $x_2$=0:

$$\sigma_{22}^1 = \sigma_{22}^f$$

$$\sigma_{12}^1 = 0$$

$$u_2^1 = u_2^f. \quad (6)$$

Applying the boundary conditions above with the potential functions in (4), the plane stress in the rigid substrate at $x_2$=h, where $E_1 = e^{i\eta_1 h}$, $B_1 = e^{i\beta_1 h}$, $E_2 = e^{-\eta_2 h}$, $B_2 = e^{-\beta_2 h}$, can be described as follows:

$$\sigma_{22}^1 = \sigma_{22}^2 \quad (7)$$

$$\sigma_{22}^1 = -\mu_1\{k_{s1}^2 \phi_1 + 2(\psi_{1,12} + \phi_{1,11})\}$$

$$\sigma_{22}^2 = -\mu_2\{k_{s2}^2 \phi_2 + 2(\psi_{2,12} + \phi_{2,11})\}$$

$$\sigma_{22}^1 = -\mu_1\{[k_{s1}^2 - k^2](a_1 E_1^{-1} + b_1 E_1) + 2k\beta_1(c_1 B_1^{-1} - d_1 B_1)\}e^{ikx_1}$$

$$\sigma_{22}^2 = -\mu_2\{[k_{s2}^2 - k^2]b_2 E_2 - 2k\beta_2 d_2 B_2)\}e^{ikx_1}$$

The shear stress at $x_2$=0 is:

$$\sigma_{12}^1 = 0$$

$$\sigma_{12}^1 = \mu_1\{2\phi_{1,12} + \psi_{1,22} - \psi_{1,11}\}$$

$$\sigma_{12}^1 = \mu_1\{2k\eta_1(a_1 - b_1) + (k^2 - \beta_1^2)(c_1 + d_1)\}e^{iks_1} = 0 \quad (8)$$

The shear stress at $x_2$=h is:

$$\sigma_{12}^1 = \sigma_{12}^2 \quad (9)$$

$$\sigma_{12}^1 = \mu_1\{2\phi_{1,12} + \psi_{1,22} - \psi_{1,11}\}$$

$$\sigma_{12}^2 = \mu_2\{2\phi_{2,12} + \psi_{2,22} - \psi_{2,11}\}$$

$$\sigma_{12}^1 = \mu_1\{2k\eta_1(a_1 E_1^{-1} - b_1 E_1) + (k^2 - \beta_1^2)(c_1 B_1^{-1} + d_1 B_1)\}e^{ikx_1}$$

$$\sigma_{12}^2 = \mu_2\{-2ik\eta_2 b_2 E_2 + (k^2 + \beta_2^2)d_2 B_2)\}e^{ikx_1}$$

The displacements along the $x_1$ direction due to the boundary condition at $x_2$=h:

$$u_1^1 = u_1^2 \quad (10)$$

$$u_1^1 = \{\phi_{1,1} + \psi_{1,2}\}$$

-continued $$u_1^2 = \{\phi_{2,1} + \psi_{2,2}\}$$

$$u_1^1 = \{ik(a_1 E_1^{-1} + b_1 E_1) + i\beta_1(-c_1 B_1^{-1} + d_1 B_1)\}e^{ikx_1}$$

$$u_1^2 = \{(ikb_2 E_2 - \beta_2 d_2 B_2)\}e^{ikx_1}$$

The plane stress in the substrate due to fluid loading at $x_2=0$ is:

$$\sigma_{22}^1 = \sigma_{22}^f \quad (11)$$

$$\sigma_{22}^1 = -\mu_1\{k_{s1}^2 \phi_1 + 2(\psi_{1,12} + \phi_{1,11})\}$$

$$\sigma_{22}^f = -\mu_f\{\phi_{2,11}\}$$

$$\sigma_{22}^1 = -\mu_1\{[k_{s1}^2 - k^2](a_1 + b_1) + 2k\beta_1(c_1 - d_1)\}e^{ikx_1}$$

$$\sigma_{22}^f = \rho_f \omega^2 m e^{n_f x_2} e^{ikx_1} = \frac{\mu_1 \rho_f k_{s1}^2}{\rho_1} m e^{ikx_1}$$

The displacement in the $x_2$ direction due to fluid loading at $x_2=0$ is:

$$u_2^1 = u_2^f \quad (12)$$

$$u_2^1 = \{\phi_{1,2} - \psi_{1,1}\}$$

$$u_2^f = \phi_{2,2}$$

$$u_2^1 = \{i\eta_1(-a_1 + b_1) + ik_1(c_1 + d_1)\}e^{ikx_1}$$

$$u_2^f = n_f m e^{n_f x_2} e^{ikx_1} = n_f m e^{ikx_1}$$

The displacement in the $x_2$ direction due to fluid loading at $x_2=h$ is:

$$u_2^1 = u_2^2 \quad (13)$$

$$u_2^1 = \{\phi_{1,2} - \psi_{1,1}\}$$

$$u_2^2 = \{\phi_{2,2} + \psi_{2,1}\}$$

$$u_2^1 = \{i\eta_1(-a_1 E_1^{-1} + b_1 E_1) + ik(c_1 B_1^{-1} + d_1 B_1)\}e^{ikx_1}$$

$$u_2^2 = \{-n_2 b_2 E_2 - ikd_2 B_2\}e^{ikx_1}$$

Assembling these equations into a system of equations the result is matrix A below. To obtain non-trivial results, the determinant of A is set to zero (det(A)=0). Using these results the dispersion curves for specified frequency ranges can be plotted.

The dispersion equation (14) can be used to quantify mechanical properties of the bladder wall, similar to the aforementioned Lamb wave dispersion described with respect to equation (2). The determinant of matrix A is set to zero and solved numerically to obtain the desired dispersion curves. Using the dispersion matrix A in UBV accounts for the media surrounding the bladder wall and provides a more complete description of the stresses and strains that affect the wave propagation in the bladder wall due to radiation force.

In addition, the bladder tissue can experience both geometric attenuation (this attenuation occurs due to boundaries in the geometry) and attenuation due to material viscosity (this attenuation would occur even if the medium was infinite). The geometric attenuation may be accounted for by using the anti-symmetric Lamb wave model, which shows significant dispersion in plates even in the absence of viscosity. The attenuation due to viscosity is accounted for by using the Voigt model to describe tissue elasticity and viscosity as two separate factors. In the case of the bladder wall, the attenuation can be significant and the waves can die out within a few centimeters from the excitation point, thereby ignoring the possible reflections and wrapping of the waves and modeling the bladder as an infinite plate, as described above. The bladder tissue may be assumed to behave as a Voigt material so that the shear modulus of elasticity $\mu=\mu_1+i\omega\mu_2$, where $\mu_1$ and $\mu_2$ are the tissue elasticity and viscosity, respectively. Other rheological models and model-free approaches for characterization of tissue mechanical properties can be used instead of the Voigt model. Tissue can be assumed to be either elastic or viscoelastic.

However, as mentioned above, other rheological models, such as Maxwell, generalized Maxwell, Zener, and the like, can be used instead of the Voigt model. Equation 3 can be fitted to obtain Lamb wave dispersion velocities, shown at process block 510, so the only inputs are the Lamb wave velocity versus frequency and the wall thickness (h) estimated from the B-mode scanning of the ultrasound system. In addition, due to the limited spatial resolution of the B-mode images, there is some error in wall thickness (h) estimates, which are used to fit the dispersion data with the Lamb wave dispersion equation (2). However, the error in Lamb wave dispersion velocity due to errors in wall thickness (h) measurements is not larger than 0.2 m/s, or around 10%. Alternatively, higher frequency ultrasound could be used to improve the accuracy of the wall thickness (h) measurements.

Figures 7A, 7B:
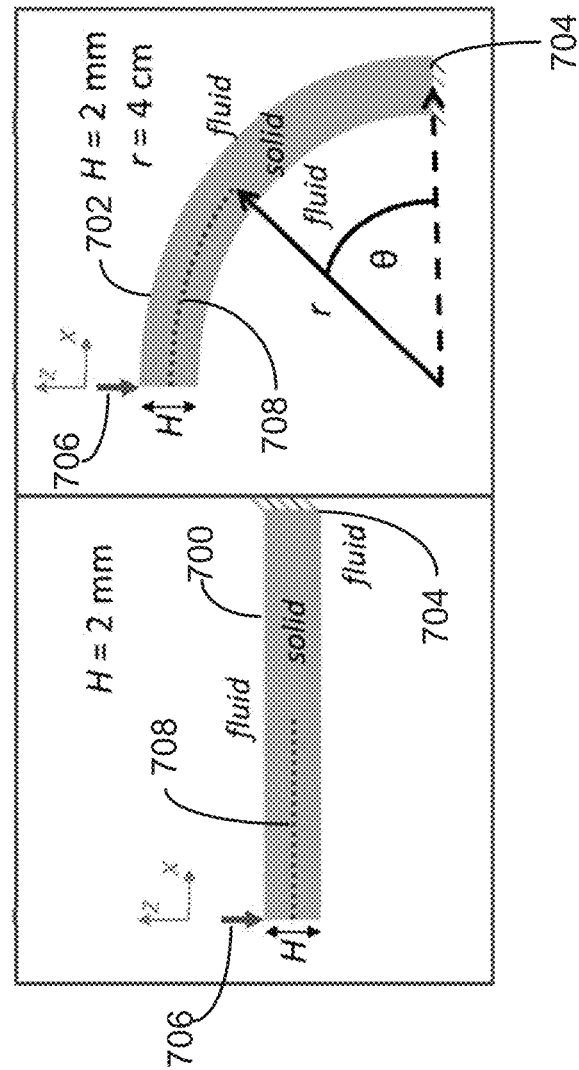
FIG. 7A is a diagram of a finite element model (FEM) of a flat viscoelastic plate submerged in a fluid of the same density.
FIG. 7B a diagram of the FEM of a curved viscoelastic plate submerged in a fluid of the same density.

Referring particularly to process block 512 of FIG. 5, finite element analysis of Lamb wave propagation in a bladder wall, modeled by a flat viscoelastic plate 700 and a curved viscoelastic plate 702, shown in FIGS. 7A and 7B, can be designed to study the effect of curvature on Lamb wave dispersion. Two-dimensional axisymmetric finite element models (FEM) of solid viscoelastic plates 700, 702 can be $$A = \begin{bmatrix} (k_{s1}^2 - k^2) & (k_{s1}^2 - k^2) & 2k\beta_1 & -2k\beta_1 & 0 & 0 & k_{s1}^2 \\ -i\eta_1 & -i\eta_1 & -ik & -ik & 0 & 0 & n_f \\ 2k\eta_1 & -2k\eta_1 & (2k^2 - k_{s1}^2) & (2k^2 - k_{s1}^2) & 0 & 0 & 0 \\ (2k^2 - k_{s1}^2)\mu_1 E_1^{-1} & (2k^2 - k_{s1}^2)\mu_1 E_1 & -2k\beta_1 B_1^{-1} & -2k\beta_1 B_1 & -(2k^2 - k_{s2}^2)\mu_2 B_2 & -2ik\beta_2 \mu_2 B_2 & 0 \\ 2k\eta_1 \mu_1 E_1^{-1} & -2k\eta_1 \mu_1 E_1 & (2k^2 - k_{s1}^2)\mu_1 B_1^{-1} & (2k^2 - k_{s1}^2)\mu_1 B_1 & 2k\eta_2 \mu_2 E_2 & -(2k^2 - k_{s2}^2)\mu_2 B_2 & 0 \\ -ikE_1^{-1} & ikE_1 & -i\beta_1 B_1^{-1} & i\beta_1 B_1 & -ikE_2 & \beta_2 B_2 & 0 \\ & & & & & & 0 \\ -i\eta_1 E_1^{-1} & i\eta_1 E_1 & -ikB_1^{-1} & -ikB_1 & \eta_2 E_2 & ikB_2 & 0 \end{bmatrix} \quad (14)$$

submerged in an incompressible urine and blood-mimicking fluid, which may be designed using ABAQUS 6.8-3 (SIMULIA, Providence, R.I.). The fluid surrounding the plates 700, 702 may be represented with acoustic elements (ACAX8) with a bulk modulus, for example, of 2.2 GPa and density, for example, of 1 g/cm$^3$. The equilibrium equation governing the inviscid fluid under the influences of small motion is:

$$\frac{\partial p}{\partial x} + \gamma \dot{u} + \rho \ddot{u} = 0, \tag{15}$$

Where p is the dynamic pressure, x is the spatial position, $\dot{u}$ and $\ddot{u}$ are the velocity and acceleration of the fluid particles, respectively and $\rho$ is the density of the fluid. $\gamma$ is defined as the "volumetric drag" in unit of force per volume per velocity. The constitutive behavior of the fluid that links the dynamic pressure p, bulk modulus K and volumetric strain $\epsilon$ is formulated as:

$$p = -K\epsilon. \tag{16}$$

The acoustic medium and solid parts are coupled with a "Tie" boundary condition and acoustic impedance, for example, at $1.5 \times 10^6$ N·s·m$^{-3}$ is prescribed to the interface.

Both the flat plate 700 and the curved plate 702 may be viscoelastic and have, for example, a density of 1.0 g/cm$^3$, Poisson's ratio of 0.499, Young's modulus of elasticity E=25 kPa and the mechanical properties defined in terms of the two-parameter Prony series where $g_1$=0.9901 and $\tau_1$=2.4× 10$^{-6}$ s, for example. The Prony series may readily be related to the generalized Maxwell model, which may further be related to the Voigt model so that the chosen mechanical properties estimate a Voigt material where $\mu_1$=8.33 kPa and $\mu_2$=2 Pa·s, for example. The plates 700, 702 can be meshed with 8-node biquadratic axisymmetric elements (CAX8H) in ABAQUS.

The flat plate 700 can be, for example, 2 mm thick and 60 mm long. The curved plate 702 can be, for example, 2 mm thick, with 4 cm inner radius, r, and 90 degrees of curvature. In both models shown in FIGS. 7A and 7B, a far end 704 of the plates 700, 702 may have a fixed boundary condition to avoid rigid motion and the plates 700, 702 may be large enough so no reflections occur. An impulsive displacement, implemented as a step function with the amplitude of 100 μm for 500 μs, for example, from a line source through the thickness of the plate, H, can be used to excite the motion in both models. The location of the excitation is noted with an arrow 706 in FIGS. 7A and 7B. The models can be solved with ABAQUS's explicit dynamic solver, as discussed previously.

The displacement can be measured, for example, every 0.5 mm along the x-axis, as shown in FIGS. 7A and 7B, at a sampling rate of 10 kHz for a total of 20 ms, for example. In the flat plate 700, the displacement can be recorded parallel to the excitation 706, which is shown along the z-axis, at, for example, 11 evenly spaced depths of the sample. In the curved plate 702, the displacement can be recorded at, for example, 11 evenly spaced depths both parallel to the excitation 706, shown along the z-axis, and perpendicular to the arc of the sample, shown along the r-axis. The middle depth line 708 can be used for analysis. The Fourier space analysis, shown at process block 508 of FIG. 5, of the displacement versus time for both plates 700, 702 can be used to obtain Lamb wave dispersion curves. The Lamb wave dispersion equation (2) with the mechanical properties inserted in the FEM simulation can be plotted for comparison. Since the UBV technique measures the axial motion on the curved surface only, the motion component parallel to the excitation 706 and linear transducer elements (not shown) can be detected. The comparison between the motion parallel to the excitation and the motion perpendicular to the arc can be carried out in order to determine whether correcting for the curvature in the displacement vector (dx=rdθ) is sufficient to account for the curvature of the plate 702.

Figure 9:
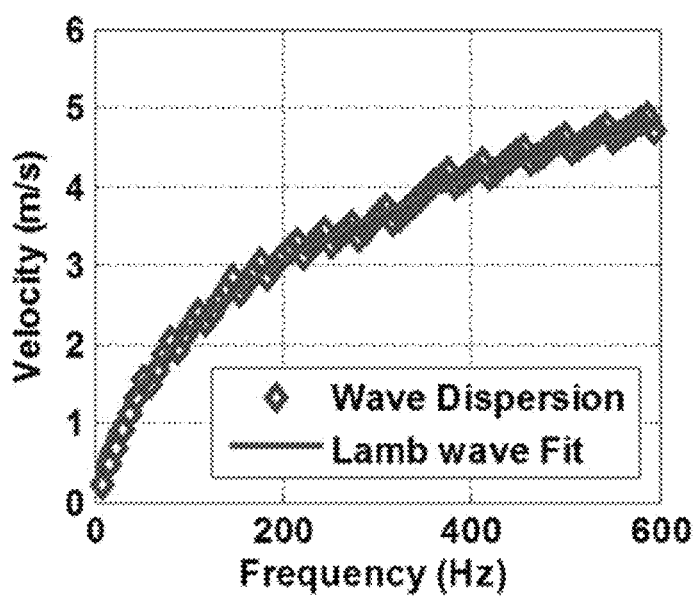
FIG. 9 is a plot of a Lamb wave dispersion equation fit to obtained dispersion data to estimate tissue elasticity according to the present invention.

Referring specifically now to process blocks 508 and 510 of FIG. 5, the impulse contains frequency components, as previously discussed. A short finite length toneburst generates frequency components up to the inverse of the time duration of the toneburst, which can facilitate extraction of many phase velocities from a single push. The impulse can propagate at a group velocity that is different from the velocities of individual frequency phase velocities and will be discussed below. Because the dispersion diagrams relate to the phase velocities, it is important to extract the phase velocities at each frequency from the impulse displacement data. As such, a two-dimensional fast Fourier transform (2D FFT) can be performed on the displacement versus time data using (6):

$$U_Z(k, f) = \sum_{m=-\infty}^{+\infty} \sum_{n=-\infty}^{+\infty} u_Z(x, t) e^{-j2\pi(kmx + fnt)}, \tag{17}$$

where $\mu_z(x,t)$ is the motion of the bladder wall perpendicular to the excitation beam 706, as shown in FIGS. 7A and 7B, as a function of distance from the excitation beam (x) and time (t). Here, k is the wave number and f is the temporal frequency of the wave. The coordinates of the k-space are the wave number (1/λ) and the frequency (f). The lowest order mode of propagation carrying the most energy is the zero-order anti-symmetric ($A_0$) Lamb wave mode. The $A_0$-mode Lamb wave phase velocity dispersion can be calculated by finding the pixel with the maximum magnitude for each frequency and, since the wave velocity c=λf, dividing the frequency coordinate (in Hz) by the wavenumber coordinate (in 1/m) of the k-space. Thus, obtained dispersion data are shown in FIG. 9. The Lamb wave dispersion equation (2) for a flat plate 700 can then be fit to the dispersion data to measure bladder elasticity and viscosity, as well as the estimated thickness of the bladder from the B-mode. In the case of the curved plate 702, the displacement vector may be constructed by recognizing that the arc length x=rθ, where r is the radius of curvature and θ the angle. This relationship corrects for the curvature of the curved plate 702.

Alternatively, the group velocity can also be used to assess the mechanical properties of the bladder. Although this method may not be as accurate as using the phase velocity to assess the mechanical properties of the bladder, as discussed previously, the advantage of this method is the simplicity in measurements and calculations. For example, the group velocity approach to assess the mechanical properties of the bladder does not require a Fourier domain analysis, shown at process block 508 of FIG. 5, as is required by the previously discussed harmonic excitation and radiation force impulse approaches. Group velocity is calculated by measuring the propagation distance of an impulse as a function of time and distance. The slope of that line is the group velocity. More specifically, one way to measure the group velocity is to measure the time that takes for the peak of the pulse to travel a known distance. This can be done by monitoring the pulse propagation in tissue. The monitoring can be done by correlating the consecutive A-line (radio frequency echo-signals) in a B-mode ultrasound of the region of interest. The time it takes the pulse to travel from its origin (where the push beam was exerted) to a point at a known distance from where the origin is measured. Alternatively, one can measure the time that takes the pulse to pass from one point in the object to another. To obtain more accurate measurements, the process can be repeated at multiple points and the group velocity can be estimated as the slope of the regression line in a distance vs. time plot.

The group velocity is then equal to the phase velocity of the center frequency of the bandwidth and is, therefore, related to the elasticity of the bladder wall. The group velocity ($c_g$) can be related to the elasticity ($\mu$) via the following equation:

$$\mu = \rho \ast (1.2 \ast c_g)^2, \tag{18}$$

where $\rho$ is the tissue density, assumed to be that of water, for example. A correction factor of 1.2 may be added to correct for the discrepancy between the shear and Lamb wave velocity.

Turning now to FIGS. 10, 11, 12, and 16, the validation of the above described UBV method for measuring viscoelasticity of the bladder wall is shown.

Figure 10:
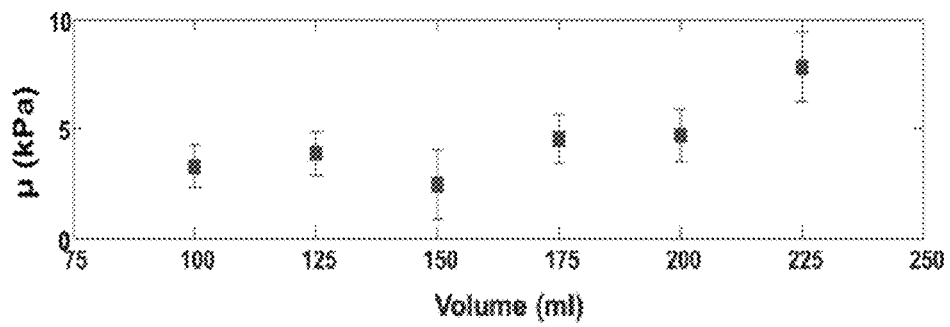
FIG. 10 is a plot of ultrasound bladder vibrometry measurements as a function of volume in a neurogenic patient of the present invention.
Figure 11:
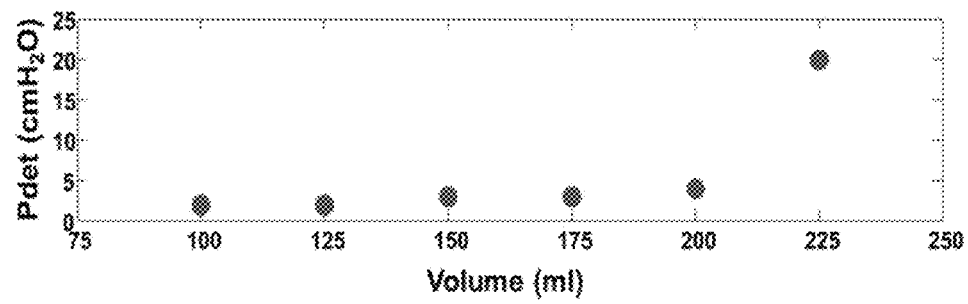
FIG. 11 a plot of urodynamic study (UDS) pressure measurements as a function of volume in a neurogenic patient.
Figure 16:
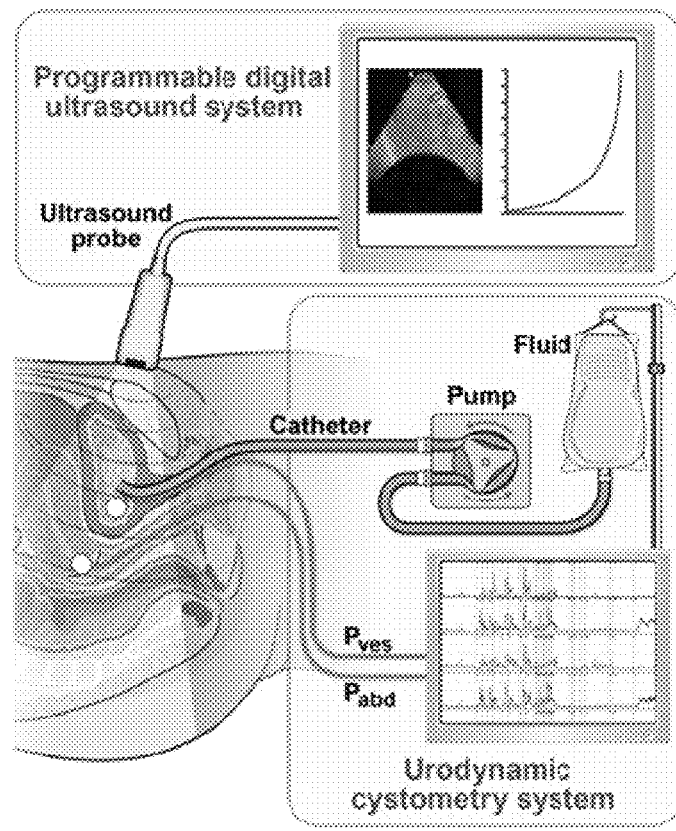
FIG. 16 presents a diagram of a hardware arrangement for the in vivo measurements according to an embodiment of the invention.

FIG. 16 illustrates schematically an embodiment for the in vivo measurements. FIG. 10 shows the results of UBV measurements in a neurogenic patient bladder as the bladder was filled in 25 mL increments. FIG. 11 shows the results of the urodynamic study (UDS) in the same neurogenic patient bladder. Comparing FIGS. 10 and 11, the UBV method and the UDS method have the same general trend as the bladder was filled in 25 mL increments, such that as the volume increased, the bladder does not readily expand causing the pressure to increase during filling. As discussed previously, the increase in pressure as the bladder is filled is representative of non-compliant bladder seen in patients with bladder dysfunction.

Figure 12:
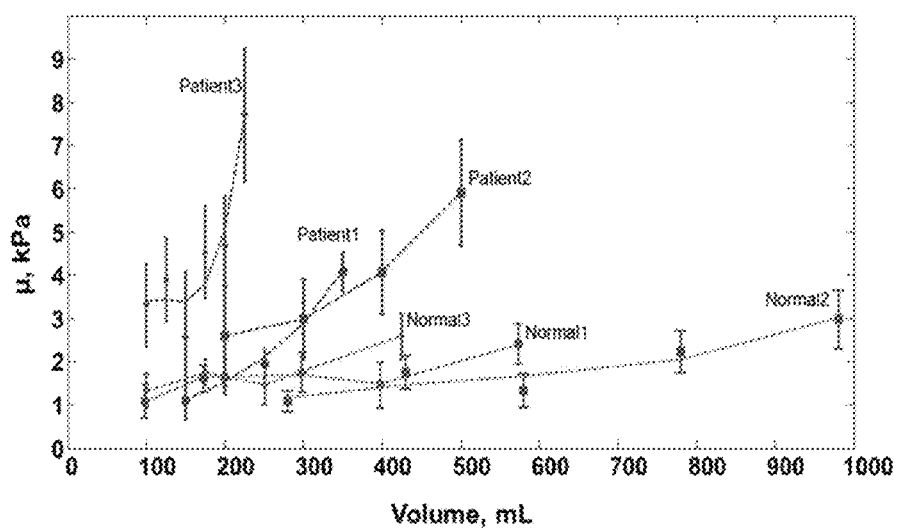
FIG. 12 is a plot of UBV measurements in patients with healthy bladders and patients with neurogenic bladders as a function of volume of the present invention.

Referring particularly to FIG. 12, the UBV estimates of elasticity ($\mu$) for three patients with normal bladders and three patients with neurogenic bladders are shown. The neurogenic bladders' elasticity show a higher increase in elasticity as a function of volume. In other words, as the bladders' volume increases, the neurogenic bladders' elasticity increases at a higher rate compared to the normal bladders' elasticity. As a result, the non-invasive UBV method can be used to determine whether a patient's bladder is healthy (compliant) or possibly diseased (non-compliant) by comparing the elasticity to that of a normal patient. In addition, the UBV method can be used as a surrogate to invasive UDS studies Another example of practical implementation of an embodiment of the invention is described in reference to FIGS. 13, 14A through 14E, and FIGS. 15A through 15C. Here, the experimental setup 1300 shown in FIG. 13 was used to measure group velocity and elasticity of an ex vivo bladder at several filling pressures and volumes, before and after formalin submersion. The filling volume for both studies was increased from 330 ml to 400 ml in 10 ml increments. The digital pressure gauge was used to measure the pressure at each volume and the UBV technique was used to measure bladder group velocity and elasticity.

Figure 14:
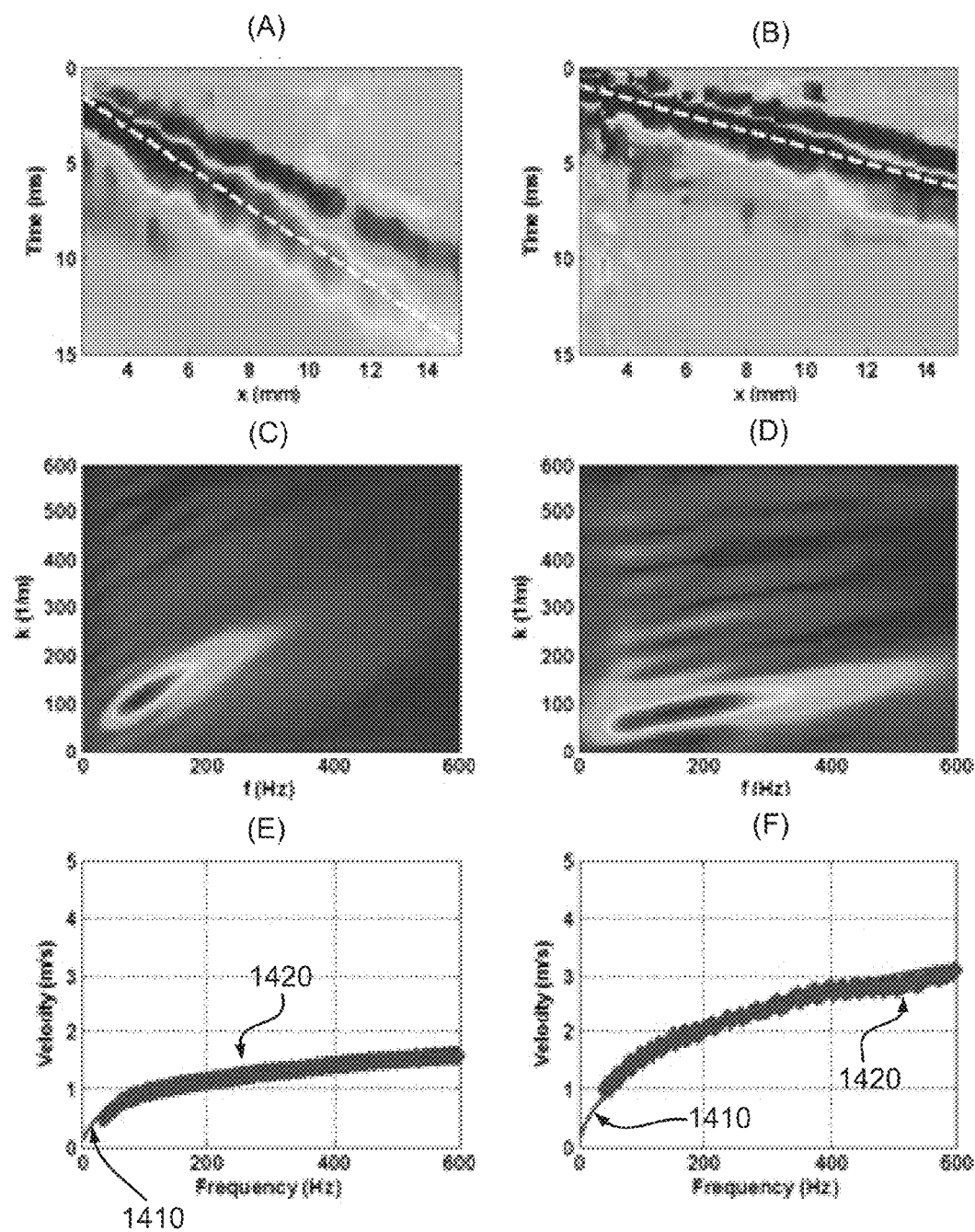
FIGS. 14A, 14B, 14C, 14D, 14E, 14F address ex vivo measurement of porcine bladder elasticity and viscosity before and after formalin treatment, with the use of the set-up of FIG. 13. Impulse propagation as a function of time and distance was used to calculate the group velocity before the treatment $c_g=dx/dt=1.03$ m/s (FIG. 14A) and after the treatment $c_g=dx/dt=3.16$ m/s (FIG. 14B); 2D FFT of the motion in FIG. 14A results in the k-space shown in FIG. 14C and 2D FFT of the motion in FIG. 14B results in the k-space shown in FIG. 14D; peak search of the k-space in FIGS. 14C and 14D yields the Lamb wave dispersion curves shown in blue in FIGS. 14E and 14F, respectively; the experimental Lamb wave dispersion curve was fit by the Lamb wave dispersion equation to estimate elasticity $\mu=2.2$ kPa in FIG. 14E and $\mu=23.9$ kPa in FIG. 14F. The bladder volume (V) was V=340 ml and the pressure (p) before formalin treatment was p=18.8 mmH$_2$O and after formalin treatment was p=19.6 mmH$_2$O.

A sample result of ex vivo bladder measurements before and after formalin treatment at the volume of V=340 ml and pressure p=18.8 mmHg inside the bladder is shown in FIGS. 14A, 14C, 14E. FIG. 14A shows the impulse propagation on the surface of the bladder as a function of time (t) and distance (x). The group velocity of the impulse can be calculated by tracking the peaks (dashed line) and calculating the slope of the line since $c_g$=dx/dt=1.03 m/s. 2D FFT of the displacement data in FIG. 14A yields the k-space shown in FIG. 14C, where the coordinates are frequency (f) and wave number (k). Since the wave velocity c=k/f; the peak-searching approach is used to obtain the experimental Lamb wave dispersion curve shown in blue in FIG. 14E. The Lamb wave dispersion equation curve shown as 1410 was fit to the dispersion data shown as 1420 to estimate bladder elasticity and viscosity. The thickness of the bladder estimated from the B-mode was 2.1 mm. The estimated excised bladder elasticity was 2.2 kPa. FIGS. 14B, 14D, 14F show the result of bladder elasticity measurements following a 120 minute formalin treatment at the volume (V) and pressure (p) of V=340 ml and p=19.6 mmHg FIG. 14B shows the impulse propagation on the surface of the bladder as a function of time (t) and distance (x) and the peak tracking method was used to calculate the group velocity $c_g$=dx/dt=3.16 m/s after formalin treatment. 2D FFT of the displacement data in FIG. 14B yields the k-space shown in FIG. 14D, and the peak-searching method is used to obtain the experimental Lamb wave dispersion curve shown in in FIG. 14F. The estimated thickness of the bladder from the B-mode was 2.0 mm and the estimated excised bladder elasticity was 23.9 kPa.

Figure 13:
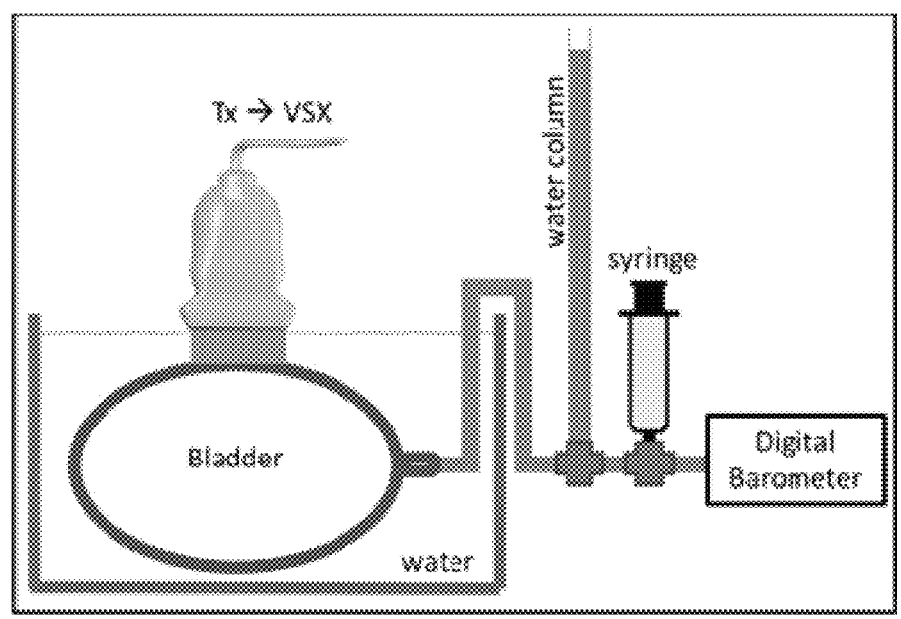
FIG. 13 shows schematically an experimental setup for the ex vivo bladder measurements uses a syringe to increase the volume inside the bladder and the digital barometer to measure the resulting pressure change. UBV measurements of group velocity, elasticity and viscosity were made at several pressures and volumes.
Figure 15:
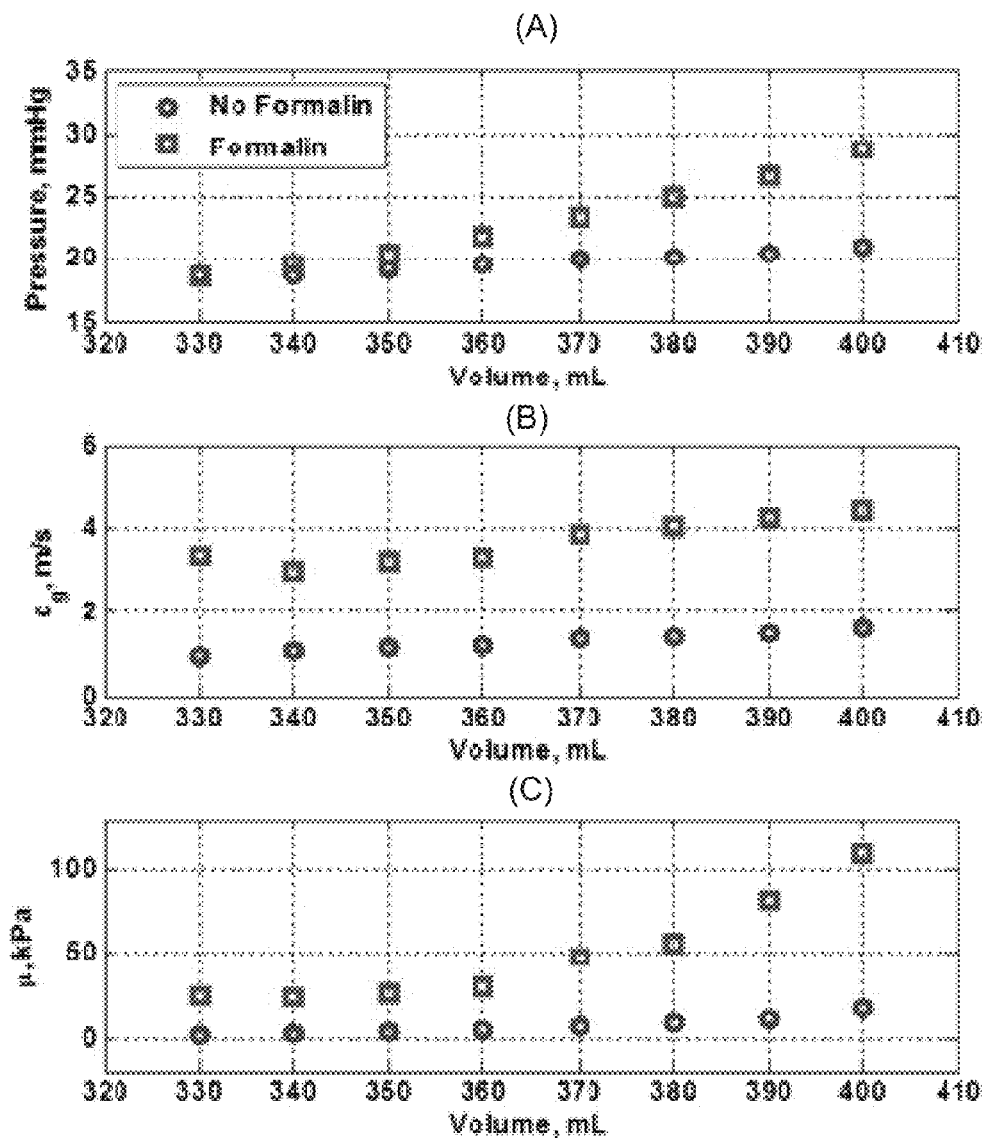
FIGS. 15A, 15B, 15C present summary of measurement data representing pressure versus volume (FIG. 14A); group velocity ($c_g$) versus volume (FIG. 15B); and elasticity ($\mu$) versus volume (FIG. 15C) acquired before and after a 120 minute formalin treatment of an excised porcine bladder sample.

The experimental setup shown in FIG. 13 was used to vary bladder pressure and volume by injecting water into the bladder with the syringe. The analysis shown in FIGS. 14A through 14F was used to measure bladder group velocity and elasticity at different pressures and volumes before and after formalin treatment in FIGS. 15A, 15B, 15C. FIG. 15A shows that the pressure inside the bladder after the formalin treatment is higher than before the formalin treatment for all volumes. In addition, the pressure versus volume curve after the formalin treatment has a significantly higher slope suggesting that formalin stiffened the tissue. FIG. 15B shows the group velocity ($c_g$) of the bladder wall versus volume before and after the formalin treatment. The group velocity following the formalin treatment is significantly higher and shows a similar pattern of increase as a function of volume. FIG. 15C shows the elasticity ($\mu$) of the bladder wall versus volume before and after the formalin treatment. FIG. 15C shows that the elasticity increased more rapidly as a function of increasing volume following the formalin treatment. Results shown in FIGS. 15, 15B, 15C demonstrate the ability of UBV technique of the present invention to delineate changes in mechanical properties of the bladder following a formalin treatment. The correlation between the $P_{det}$ pressure and the group velocity as well as between the pressure and elasticity as a function of volume in an excised porcine bladder is fair. These results suggest that both group velocity and the elasticity can be used as surrogates for the intra-bladder pressure.

The correlation between the intra-bladder pressure and the group velocity and elasticity of the bladder was further explored. Pressure, group velocity and elasticity values as a function volume were normalized by dividing with the values at V=400 ml. The $R^2$ for correlation between normalized pressure and normalized group velocity before the formalin was $R^2$=0.9684, between normalized pressure and elasticity before formalin treatment $R^2$=0.9400. The $R^2$ for correlation between normalized pressure and normalized group velocity after the formalin was $R^2$=0.8919, between normalized pressure and elasticity after formalin treatment $R^2$=0.9275.

As previously discussed, increase in bladder stiffness may be associated with various pathophysiologic conditions. Measuring bladder viscoelasticity can provide clinically-useful information regarding various disease processes and, thereby, improve patient care. Hence, the disclosed ultrasound bladder vibrometry (UBV) is an advantageous method for rapid, relatively pain-free, and non-invasive measurement of tissue wall viscoelasticity.

Another important advantage of UBV is the use of Lamb waves, rather than shear waves, to characterize the motion of the wall due to radiation force. The tissue walls can be fairly thin so the compressional and shear waves are not separable and combine to form the Lamb waves. The Lamb wave model has been used before to characterize mechanical properties of soft tissues with plate-like geometry, but not plate-like geometry surrounded by connective tissue, fat and peritoneal fluid on one side, as is the case in the disclosed UBV technique.

Figure 17:
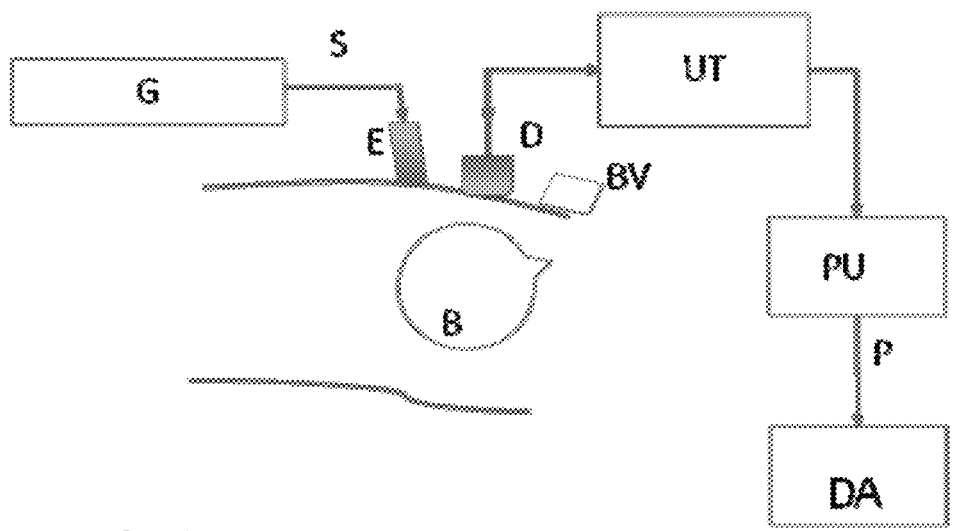
FIG. 17 is a schematic diagram illustrating a particular implementation of method and system of the invention.

Additional schematic representation of a system for performing bladder compliance measurements is shown in FIG. 17. The system employs an excitation unit (which may include an exciter E, driven by a signal generator G) that in operation induces a force on the bladder that results a wave motion propagating through the bladder wall. The system further employs an ultrasound detector unit D operable to detect such wave motion, and, optionally, a pulse echo ultrasound tracking unit UT that governs the operation of the detector D and receives an output from the detector to track wave motion in the bladder wall. The system also includes data processing unit or processor PU structured to calculate one or more parameter P representing a mechanical property or characteristic of the bladder. The system may further include a data collection and data analyzer unit DA for correlating the parameter P with different bladder volumes. Alternatively or in addition, the system may include a device BV for measuring bladder volume at each volume setting. The exciter E may include a vibrator that operates based on electro-mechanical, mechanical, or piezoelectric principles, and which, in operation, employs a vibrator head that is placed on the body of the subject to transfer vibration to the bladder. The exciter E may be driven by a signal S (in the form of a single frequency tone burst, at desired frequencies; or, in the form of a short pulse generating a transit signal, for example). The exciter E may include an ultrasound transducer (whether in the form of a single element, multi-element, or an array of elements) that in operation is placed on the body of the subject to transfer ultrasound energy to the bladder through the subject's tissue. The generator G may include a single generator or (if the exciter E has multiple transducer elements) multiple signal generators to produce multiple signals (collectively denoted by S), and a beam former, similar to those used in medical ultrasound scanners, to feed the elements of the transducer in a fashion that results in a formation of an ultrasound beam applying a radiation force on the bladder B. The signal S may include one ore multiple short pulses or one or more sinusoidal tone bursts at one or more frequencies. In a specific case, the generator G is operable to produce two simultaneous sets of signals S at two slightly different frequencies, and the exciter E produces two intersecting ultrasound beams to form a radiation force (applied to the bladder B) at the beat frequency of these different frequencies. Generally, the processing unit PU uses the information from ultrasound echoes from received from the tracking unit UT to detect a motion of the bladder wall. According to a method of the invention, the motion of the bladder motion may be calculated based on temporal variations of the ultrasound echoes reflected from the bladder wall and, in particular, with the use of Lamb wave model and/or determination of a dispersion curve of either group or phase velocity of the wave motion propagating along the wall of the bladder. Based on such dispersion data, the elasticity and/or viscosity of the bladder wall is further determined, with or without the use of a rheological model (such as Kelvin-Voigt, Zener, or Maxwell model, for example). The processor PU may be further programmed to correlate the changes in wave velocity(ies) and/or bladder elasticity or viscosity with the internal pressure (Pb) of the bladder caused by liquid inside the bladder at different bladder volumes, and further to correlate the parameter P with the pressure on the bladder detrusor urinae muscle (Pdet). Detrusor pressure ($P_{ad}$) is calculated by subtracting the abdominal pressure ($P_{abd}$, measured with a rectal catheter) from the vesical pressure ($P_{ves}$, measured with a catheter in the bladder): $P_{det}=P_{ves}-P_{abd}$. The procedure of correlation between the parameter P and Pb or Pdet is further used to determine the response of bladder to incremental increase in liquid volume in the bladder. The parameter P, and/or the values of Pb and/or Pdet are further used to calculate the bladder compliance C to provide early signs of changes in bladder abnormalities, including bladder non-compliance, before the clinical signs appear. According to the idea of the invention, the described method and system can be used as a diagnostic predictor allowing early and improved treatment which is not possible by current clinical diagnostic methods.

It is understood that a method and system for evaluating mechanical compliance of a bladder may require the use of a data-processing electronic circuitry (a processor) controlled by instructions stored in a tangible, non-transient memory. The memory may be random access memory (RAM), read-only memory (ROM), flash memory or any other memory, or combination thereof, suitable for storing control software or other instructions and data. Those skilled in the art should also readily appreciate that instructions or programs defining the functions of the present invention (such as collection and/or storing of experimental data; data processing to define the sought-after parameters, for example) may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including wired or wireless computer networks. In addition, while the invention may be embodied in software, the functions necessary to implement the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components. Accordingly, system and method employing a processor specifically programmed to perform the steps of the method of the invention and computer program product containing the set of instructions governing the processor to perform such steps are within the scope of the invention.

The present invention has been described in terms of one or more preferred embodiments, and it should be appreciated that many equivalents, alternatives, variations, and modifications, aside from those expressly stated, are possible and within the scope of the invention. For example, although the method of the invention as described was based on spectral analysis of the ultrasound echo data, it is appreciated that a time-domain analysis can be alternatively employed to determine the dispersion data. In one example, the group velocity or the velocity of the wave peak can be correlated with bladder muscle pressure. Similarly, the complex propagation of a mechanical wave in a soft tissue can be approximated with a shear-wave model (based on consideration of a wave for which the displacement of object particles is perpendicular to the direction of wave propagation, and by definition there are no boundaries in the medium that would affect such propagation) or with a wave model based on the Lamb wave (which is defined for the wave propagates along a plate, or parallel to the surface, with particles moving perpendicularly to the plate surface and, therefore, perpendicularly to the wave propagation direction). In the Lamb-wave based model, the two surfaces of the (infinite) plate are the boundaries that guide the wave forward. In the case of waves propagating on the bladder wall, as in embodiments of the present invention, a Lamb wave model provides a practical and good approximation. However, one generally may also use other wave models with an embodiment of the invention (such as shear wave model referred to above) to approximate the wave motion on the bladder.

The determination of whether the bladder is compliant or non-compliant can be determined as follows: if the measured parameter P (e.g., elasticity or group velocity) changes extensively when the bladder volume changes from almost empty to almost full, then the bladder is non-compliant (or poorly-compliant). If the measured parameter P changes insignificantly when the bladder volume changes from almost empty to almost full, then the bladder is compliant. The measurements can be performed in a clinic without using a catheter to fill the bladder. In this case, the patient is asked to come with a full bladder. The ultrasound measurements are taken once, after which the bladder is partially emptied (in a graduated container) and the urine volume in the container is recorded. Then ultrasound measurements are made again. The cycle is repeated until the bladder is completely emptied. This way, the ultrasound measurements are taken at multiple bladder volumes. A plot of parameter P versus bladder volume is created, and if the measured parameter P is much higher at large volume of the bladder than at the low volume(s) of the bladder, then the bladder is considered to be non-compliant.

What is claimed is:

1. A method for characterizing a parameter representing a mechanical property of a tissue wall, the method comprising:
   with a transducer, detecting ultrasonic energy reflected by multiple locations along the tissue wall that is subject to stress to form ultrasonic echo data, wherein said tissue wall having geometric boundaries and defining a volume enclosed by the tissue wall, said tissue wall separating a fluid material contained in said volume from a rigid material outside of the tissue wall, and
   determining dispersion data representing a mechanical deformation of said tissue wall from said echo data.

2. A method according to claim 1, wherein said determining includes
   calculating a dispersion characteristic of phase velocity of said mechanical deformation propagating along the tissue wall, and
   fitting said dispersion characteristic with an anti-symmetric Lamb wave or shear-wave function to account for attenuation, of said mechanical deformation in the tissue wall, that is caused by said geometric boundaries.

3. A method according to claim 2, further comprising causing said mechanical deformation by applying an excitation input to said tissue wall along a direction of excitation.

4. A method according to claim 2, wherein said tissue wall is spatially curved, wherein said fitting includes introducing a correction for a spatial displacement caused by said mechanical deformation and associated with a curvature of said tissue wall, said correction being a result of comparison between a first motion of the tissue wall and a second motion of the tissue wall, the first motion occurring in a direction parallel to the excitation direction, the second motion occurring perpendicularly to a surface of said curved tissue wall.

5. A method according to claim 1, wherein said determining includes spectrally analyzing said echo data to determine dispersion data representing said mechanical deformation, which mechanical deformation corresponds to a motion of a spatially curved tissue wall along a surface of said tissue wall.

6. A method according to claim 1, wherein said determining includes calculating a dispersion characteristic of phase velocity of said mechanical deformation, which propagates along the tissue volume, with the use of a rheological function to account for attenuation, of said mechanical deformation in the tissue wall, that is caused by viscosity of the tissue wall.

7. A method according to claim 6, wherein said calculating includes calculating said dispersion characteristic with the use of a rheological function employing elasticity of said tissue wall and viscosity of said tissue wall as separate factors.

8. A method according to claim 1, wherein said detecting ultrasonic energy includes causing said stress by applying to the tissue wall at least one of (i) an acoustic radiation force, (ii) an electro-mechanical input; and (iii) a mechanical input.

9. A method according to claim 1, wherein said tissue wall is spatially curved, and further comprising estimating a viscoelasticity parameter of said tissue wall with the use of Lamb-wave or shear-wave calculation based on said dispersion data.

10. A method according to claim 1, further comprising determining, based on the dispersion data, said parameter representing a mechanical property of the tissue wall in association with pressure produced by said tissue wall onto said fluid material, wherein said parameter representing a mechanical property of the tissue wall includes one or more of: (i) a phase velocity of a wave associated with said mechanical deformation, (ii) a group velocity of a wave associated with said mechanical deformation; (iii) a wave-peak velocity associated with said mechanical deformation; (iv) elasticity of the tissue wall, (v) a viscosity of the tissue wall, and (vi) compliance of the tissue wall.

11. A method according to claim 1, wherein said determining dispersion data includes performing spectral analysis of said echo data, and tissue wall includes a wall of a bladder of a living subject.

* * * * *